(12) United States Patent
Ruan et al.

(10) Patent No.: US 9,644,233 B2
(45) Date of Patent: May 9, 2017

(54) LOOP-SHAPED PRIMER USED IN NUCLEIC ACID AMPLIFICATION AND THE USE THEREOF

(75) Inventors: Li Ruan, Xiamen (CN); Donghua He, Xiamen (CN); Limou Zheng, Xiamen (CN); Yan Chen, Xiamen (CN)

(73) Assignee: XIAMEN AMOY DIAGNOSTICS CO., LTD., Xiamen (CN)

( * ) Notice: Subject to any disclaimer, the term of this patent is extended or adjusted under 35 U.S.C. 154(b) by 444 days.

(21) Appl. No.: 13/142,874

(22) PCT Filed: Mar. 26, 2009

(86) PCT No.: PCT/CN2009/071026
§ 371 (c)(1),
(2), (4) Date: Jun. 30, 2011

(87) PCT Pub. No.: WO2010/108325
PCT Pub. Date: Sep. 30, 2010

(65) Prior Publication Data
US 2011/0269192 A1    Nov. 3, 2011

(51) Int. Cl.
  *C12Q 1/68*    (2006.01)
(52) U.S. Cl.
  CPC .................................. *C12Q 1/686* (2013.01)
(58) Field of Classification Search
  None
  See application file for complete search history.

(56) References Cited

U.S. PATENT DOCUMENTS

2005/0266418 A1*  12/2005  Chen et al. .................. 435/6
2009/0023190 A1    1/2009  Lao et al.

FOREIGN PATENT DOCUMENTS

| CN | 1420928 A   |   | 5/2003  |           |
|----|-------------|---|---------|-----------|
| CN | 1712546 A   |   | 12/2005 |           |
| CN | 1836050 A   |   | 9/2006  |           |
| CN | 101076608 A |   | 11/2007 |           |
| JP | EP1988178   | * | 11/2008 | C12Q 1/68 |

OTHER PUBLICATIONS

Tong et al. (Clin Chem, 2007, 53(11):1906-1914).*
(Continued)

*Primary Examiner* — Stephanie K Mummert
(74) *Attorney, Agent, or Firm* — Rabin & Berdo, P.C.

(57) ABSTRACT

Loop-shaped primer used in nucleic acid amplification is an oligonucleotide with 3-20 bases in both 3' and 5' ends which can be combined together to form a double-strand under appropriate conditions, resulting in the primer forming a stem-loop structure. The double-stranded structure is opened and the stem-loop structure dissolves when the primer recognizes and hybridizes with the target sequence. If the target sequence is not present the primer can form a stem-loop structure automatically by self-annealing. The primer can comprise a universal tag sequence or not. Together with universal tag sequence primer the primer comprising the universal tag sequence can be used for a second round of amplification. The primer has high specificity and does not form a primer dimmer. The primer is easy to design and is suitable for measuring gene expression and detecting features of nucleic acids such as SNPs and rare mutations.

12 Claims, 8 Drawing Sheets

(56) References Cited

OTHER PUBLICATIONS

Beuvink et al. (Nucleic Acids Research, 2007, 35(7):e52, p. 1-11).*
Nagamine et al. (Molecular Cellular Probes, 2002, vol. 16, p. 223-229, IDS reference).*
Ailenberg et al. (Biotechniques, 2000, 29:1018-1024).*
Brownie et al. (Nucleic Acids Research, 1997, 25(16):3235-3241).*
Kaboev et al. (Nucleic Acids Research, 2000, 28(21):e94).*
Kaboev et al. Bioorg Khim. May 1999;25(5):398-400, Abs.*
Yang Xu et al., "Stem-loop Structured Probes Designed by Sequence Comparisons for Detection of Staphylococcus aureus", Microbiology, ISSN:0253-2654, vol. 34, No. 06, pp. 1169-1173, Dec. 31, 2007(Dec. 31, 2007).
Yi, Haihua et al., "Detecting My cobacterium Tuberculosis in Sputum Specimens by Technique of Loop-mediated Isothermal Amplification", Chinese Journal of Frontier Health and Quarantine, ISSN: 1004-9770, vol. 31, No. 01, pp. 7-11 and 17, Feb. 29, 2008(Feb. 29, 2008).
Weihong Tan et al., "Molecular beacons", Current Opinion in Chemical Biology, 2004, (8): 547-553, Dec. 31, 2004(Dec. 31, 2004).
K. Nagamine et al., "Accelerated reaction by loop-mediated isothermal amplification using loop primers", Molecular and Cellular Probes, 2002(16): 223-229, Dec. 31, 2002 (Dec. 31, 2002).

* cited by examiner

SEQUENCE LISTING

```
<160> NUMBER OF SEQ ID NOS: 15

<210> SEQ ID NO 1
<211> LENGTH: 28
<212> TYPE: DNA
<213> ORGANISM: Artificial Sequence
<220> FEATURE:
<223> OTHER INFORMATION: Synthesized

<400> SEQUENCE: 1
aaccagctca tcgtcgctgg agctggtt                                            28

<210> SEQ ID NO 2
<211> LENGTH: 29
<212> TYPE: DNA
<213> ORGANISM: Artificial Sequence
<220> FEATURE:
<223> OTHER INFORMATION: Synthesized

<400> SEQUENCE: 2
atcagcttgc ggcggtttgt caagctgat                                           29
```

<210> SEQ ID NO 3
<211> LENGTH: 29
<212> TYPE: DNA
<213> ORGANISM: Artificial Sequence
<220> FEATURE:
<223> OTHER INFORMATION: Synthesized

<400> SEQUENCE: 3
ggtcctacaa catcaggatt cctaggacc                                    29

<210> SEQ ID NO 4
<211> LENGTH: 26
<212> TYPE: DNA
<213> ORGANISM: Artificial Sequence
<220> FEATURE:
<223> OTHER INFORMATION: Synthesized

<400> SEQUENCE: 4
caacctcggt gagtgattgg aggttg                                       26

<210> SEQ ID NO 5
<211> LENGTH: 26
<212> TYPE: DNA
<213> ORGANISM: Artificial Sequence
<220> FEATURE:
<223> OTHER INFORMATION: Synthesized

<400> SEQUENCE: 5
cagagtctag actcgtggtg gacttc                                       26

<210> SEQ ID NO 6
<211> LENGTH: 31
<212> TYPE: DNA
<213> ORGANISM: Artificial Sequence
<220> FEATURE:
<223> OTHER INFORMATION: Synthesized

<400> SEQUENCE: 6
cgcatctgac caagctggcc acccagatgc g                                 31

<210> SEQ ID NO 7
<211> LENGTH: 31
<212> TYPE: DNA
<213> ORGANISM: Artificial Sequence
<220> FEATURE:
<223> OTHER INFORMATION: Synthesized

<400> SEQUENCE: 7
cgcatctgac caagctggcc acccagatgc a                                 31

<210> SEQ ID NO 8
<211> LENGTH: 17
<212> TYPE: DNA
<213> ORGANISM: Artificial Sequence
<220> FEATURE:
<223> OTHER INFORMATION: Synthesized

<400> SEQUENCE: 8
tgccccgaag ccaatcc                                                 17

<210> SEQ ID NO 9
<211> LENGTH: 52
<212> TYPE: DNA
<213> ORGANISM: Artificial Sequence
<220> FEATURE:
<223> OTHER INFORMATION: Synthesized

```
<400> SEQUENCE: 9
acaagctccg caaggggtca gtaaagcgaa acttgtggta gttggagctt gt          52

<210> SEQ ID NO 10
<211> LENGTH: 39
<212> TYPE: DNA
<213> ORGANISM: Artificial Sequence
<220> FEATURE:
<223> OTHER INFORMATION: Synthesized

<400> SEQUENCE: 10
gcaaggggtc agtaaagcgt cgtccacaaa atgattctg                         39

<210> SEQ ID NO 11
<211> LENGTH: 19
<212> TYPE: DNA
<213> ORGANISM: Artificial Sequence
<220> FEATURE:
<223> OTHER INFORMATION: Synthesized

<400> SEQUENCE: 11
gcaaggggtc agtaaagcg                                               19

<210> SEQ ID NO 12
<211> LENGTH: 18
<212> TYPE: DNA
<213> ORGANISM: Artificial Sequence
<220> FEATURE:
<223> OTHER INFORMATION: Synthesized

<400> SEQUENCE: 12
tgccttgacg atacagct                                                18

<210> SEQ ID NO 13
<211> LENGTH: 39
<212> TYPE: DNA
<213> ORGANISM: Artificial Sequence
<220> FEATURE:
<223> OTHER INFORMATION: Synthesized

<400> SEQUENCE: 13
gcaaggggtc agtaaagcgg cagtgccttc ccaaccatt                         39

<210> SEQ ID NO 14
<211> LENGTH: 43
<212> TYPE: DNA
<213> ORGANISM: Artificial Sequence
<220> FEATURE:
<223> OTHER INFORMATION: Synthesized

<400> SEQUENCE: 14
gcaaggggtc agtaaagcgc attccccaag agcttacaaa ctc                    43

<210> SEQ ID NO 15
<211> LENGTH: 20
<212> TYPE: DNA
<213> ORGANISM: Artificial Sequence
<220> FEATURE:
<223> OTHER INFORMATION: Synthesized

<400> SEQUENCE: 15
ttgacaacgc tatgctccgc                                              20
```

LOOP-SHAPED PRIMER USED IN NUCLEIC ACID AMPLIFICATION AND THE USE THEREOF

FIELD OF THE INVENTION

The invention relates to the design and application of the amplification of nucleic acid of polymerase chain reaction (PCR), more particularly, to application for Real-Time PCR, especially to the application for detection of mutations and rare mutations.

BACKGROUND OF THE INVENTION

Polymerase chain reaction (PCR) is a gene amplification method with a simple process, high sensitivity and excellent specificity. Generally, the process is comprised of 20-50 cycles each having three steps: denaturation, annealing and extension. The target nucleic acid can be amplified to millions of times its original concentration in 1.5-3 h. In recent years, real-time PCR amplification has made gel electrophoresis of PCR products unnecessary, thus the post-manipulation of PCR products is not needed, and opportunities for PCR contamination are prevented. Because of these advantages, real-time PCR is used more and more widely. Originally, real-time PCR is used with fluorescent dyes, such as SYBR GREEN, EVE GREEN etc., to detect the PCR product. More recently, nucleic acid probes with fluorescent labels are applied in real-time PCR, such as Taqman probe, molecular beacon, fluorescence resonance energy transform probe, scorpion primers, probes etc. used in 5'-exonuclease technology, Although PCR based on fluorescent dyes is simple, it can not identify the nonspecific amplification, especially the nonspecific amplification caused by primer dimers, so it has many limitations in application. A probe provides a second identification step for the amplification products, therefore the nonspecific amplification is prevented, so its result is more reliable. But the probe has disadvantages such as complex design and high synthetic cost etc. The shortcomings of the two methods are based on the fact that they can not prevent nonspecific amplification.

Rare mutations refer to mutant alleles that are present at a relatively low concentration, or copy number, compared to normal alleles. It especially refers to genes with a single base mutation. Generally, the ratio of mutation gene to wild-type gene is less than $1/1000$, for example, trace embryo mutant gene contained in the blood of pregnant woman, or tumor cell-derived mutant DNA contained in blood or tumor tissue of a cancer. The detection of these rare mutations can be a challenge for the detection technologies of the prior art.

The key to successful PCR applied to mutation detection is to design a pair of primers with high precision and complementary to target gene DNA or RNA. Amplification Refractory Mutation System, ARMS was invented in 1989, it is also called Allele-specific PCR (AS-PCR) or PCR with Sequence Specific Primers (PCR-SSP). It has the widest use of any mutation detection method. The basic idea is to design two forward ARMS primers, which have a common reverse primer to form a PCR system. The specific base of allele gene is set in the 3' end of the primer, this is because the Taq DNA polymerase does not have 3'-5' exonuclease proofreading activity, in PCR, the specific base in the 3' end of the primers combine to the sites of wild-type or mutation allele gene; if the base is mismatched, the DNA extension reaction will fail due to the inability to form the 3'-5'-phosphodiester linkage. However, the base of 3'end of ARMS primers has limited ability differentiate between different mismatchs, thus they have limited ability to differentiate some mutations.

SUMMARY OF THE INVENTION

The invention relates to a novel primer for amplification of nucleic acid. The primer of the invention has a different design concept compared to prior primers. By incorporating novel design features, the specificity of the primer is improved markedly. The primer of the invention has high specificity and simple design, does not form primer dimers, and is suitable for quantitating gene expression levels and detecting SNPs and rare mutations.

The primers of the invention comprises two types, One is a single loop-shaped (or annular) primer which can be used in general amplification of nucleic acid; the other is double amplification loop-shaped primers which can be especially used in mutation detection system, especially for rare mutation detection system.

The single loop-shaped primer technology of the present invention is based on direct hybridization to the target nucleic acid, the 5' end has complementary sequence to the 3' end, so the primer can form a loop-shaped structure, and the loop-shaped structure is easy to be opened, so the amplification efficiency to the target sequence will not be affected. The bases to the mutation sequence can be set to the 3' end or inside of primer, the length of the loop-shaped sequence can be adjusted according to different sequences, thus the specificity of the primer to the mutation sequence can be adjusted.

The double amplification loop-shaped primers of the invention provide a universal tag sequence inside of the primer, the tag sequence and the loop-shaped primer are input to a PCR amplification system in a certain concentration (generally, the tag sequence is more than 10 times of the loop-shaped primers), in the early two cycles of PCR, the loop-shaped primer recognizes the mutation target sequence with high specificity and process earlier amplification, from the third cycle, because the larger amount of the label primer, the PCR products of the earlier stages will be amplified greatly and rapidly by the tag primer, thus maintaining high specificity and sensitivity to rare mutation target sequence.

Therefore, the loop-shaped primers of the invention can be used to detect the target nucleic acid in real-time PCR.

The nucleotide of the primer of the invention can be DNA, RNA, LNA or PNA, or a non-natural nucleotide.

The invention also relates to the application of the loop-shaped primer.

The invention relates to a novel primer for nucleic acid amplification of PCR. The primer is an oligonucleotide, and the 5' end and the 3' end has 3-20 complementary bases respectively, in certain conditions they can form a double-strand to make the primer a loop-shaped structure, the base that recognizes and anneals with the mutation can be set in the first base of the 3' end or inside the primer. In certain conditions, the 3' end forms a double-strand, and the inside of the primer form an loop-shaped structure, when the primer is recognized and hybridized to the target sequence, the double-strand structure is opened and the loop-shaped structure is miss, and the double-strand of the primer is transformed to be the double-strand combined with the target sequence, thus acquiring DNA extension ability. If the target sequence is not present, the primer can form a loop-shaped structure in the annealing step, the 3' end is forms a double-strand to stop the 3' end DNA extension ability, thus the nonspecific amplification (especially primer dimers) will not be produced. Referring to FIG. 1a and FIG. 1b.

Referring to FIG. 1a, the single loop-shaped primer system has two primers: single amplification forward primer F and single amplification reverse primer R. The forward primer has three different domains 31, 32 and 33, herein the domain 31 is named target recognizing domain, 32 is named mutation recognizing domain, the mutation recognizing domain can be set in the 3' end or away to the 3' end, this can be set according to different types of rare mutations; the domain 33 is named complementary sequence. In a preferred embodiment, the reverse primer R comprises two functional domains 34 and 35, herein the domain 34 is named to be target recognizing domain, domain 35 is named to be complementary sequence.

FIG. 1b shows that the process of amplification of the target mutation sequence by the primer of the present invention, which effectively solve the problem of primer dimers produced by SNP, common PCR detection and multiplex PCR. In common conditions, the forward primer and reverse primer form a loop-shaped structure, thus avoid producing primer dimers. Only in the denaturation step, the loop-shaped structure is opened and combined to the target sequence in annealing, referring to the figure, the forward primer is combined with the target mutation sequence 41 and the reverse primer combined with target sequence 42, the products 43, 44 are obtained by extension. The sequence 43 is then to be the target sequence of the reverse primer, the reverse primer combined to the product sequence 43 to obtain object product 45.

The invention also provides a novel primer for PCR detection and real-time PCR detection of the gene mutation, especially to rare mutation. The primer is an oligonucleotide, and the 5' end and the 3' end have 3-20 complementary bases, in certain conditions they can form a double-strand to make the primer a loop-shaped structure, and the inside of the primer has an universal tag sequence, the recognizing base can be set in the first base of the 3'end or inside the primer. In certain conditions, the 3' end forms an intra-molecular double-strand, and the inside of the primer forms an loop-shaped structure; when the primer recognizes and hybridizes to the target sequence, the intra-molecular double-strand structure is opened and the loop-shaped structure is lost, and the double-strand of the primer is transformed to be the double-strand combined with the target sequence, thus acquiring DNA extension ability. The label sequence and the loop-shaped primer are input to a PCR amplification system in an appropriate concentration (generally, the tag sequence is more than 10 times of the loop-shaped primers), in the early two cycles of PCR, the loop-shaped primer recognize the mutation target sequence with high specificity and process earlier amplification, from the third cycle, because the larger amount of the tag primer, the PCR products of the earlier stages will be amplified greatly and rapidly by tag primer, thus maintaining high specificity and sensitivity to rare mutation target sequence. If there is no target sequence present, the primer can form a loop-shaped structure in the annealing step; since the 3' end is formed into an intra-molecular double-stranded structure, the 3' end can not initiate DNA extension, thus nonspecific amplification (especially primer dimers) will not be produced. The recognizing base for the mutation sequence can be set to the 3' end or inside the primer according to the specialty of the target sequence. The specificity of the primer can be adjusted by the length of the double-strand in the 3' end of the primer itself, when the target sequence has one or more bases mismatch to the primer, the loop-shaped structure of the primary cant be opened, the double-strand structure in the 3' end of the primer will be existed, and this stop the 3' end extension ability, thus the amplification will not begin Referring to FIG. 2a and FIG. 2b.

Structure of Loop-Shaped Primer

The loop-shaped primers of the invention comprises two designs for different needs, one is single amplification loop-shaped primer for general gene amplification which can avoid primer dimers; the other is double amplification loop-shaped primer for detecting rare mutation with high specificity.

Single amplification loop-shaped primer. The primer is an oligonucleotide, and the 5' end and the 3' end has 3-20 complementary bases respectively, in certain conditions the 3' end of the primer can form an intra-molecular double-strand, and the inside of the primer forms a loop-shaped structure; when the primer is recognizes and hybridizes to the target sequence, the double-stranded structure is opened and the loop-shaped structure is lost, and the double-strand of the primer is transformed to the double-strand combined with the target sequence, thus acquiring DNA extension ability. If there is no target sequence present, the primer can form loop-shaped structure in annealing step, the 3' end is formed double-strand to stop the 3' end DNA extension ability, thus the nonspecific amplification (especially primer dimers) will not be produced. Referring to FIG. 1a and FIG. 1b.

Double amplification loop-shaped primer. The primer is a single oligonucleotide, and the 5' end and the 3' end has 3-20 complementary bases, in appropriate conditions they can form a double-strand to make the primer a loop-shaped structure, and the inside of the primer has a universal tag sequence, the distinguishing base can be set in the first base of the 3' end or inside the primer. In appropriate conditions, the 3' end may form an intramolecular double-strand, and the inside of the primer forms a loop-shaped structure; when the primer recognizes and hybridizes to the target sequence, the double-strand structure is lost, and the primer forms a double-strand with the target sequence, thus acquire DNA extension ability. The tag sequence and the loop-shaped primer are input to a PCR amplification system in a certain concentration (generally, the tag primer is more than 10 times to the loop-shaped primers), in the early two cycles of PCR, the loop-shaped primer recognizes the mutation target sequence with high specificity and process earlier amplification, from the third cycle, because the larger amount of the tag primer, the PCR products of the earlier stages will be amplified greatly and rapidly by the tag primer, thus maintaining high specificity and sensitivity to rare mutation target sequence. If there is no target sequence present, the primer can form loop-shaped structure in annealing step, the 3' end form double-strand to stop the 3' end DNA extension ability, thus the nonspecific amplification (especially primer dimers) will not be produced. The recognizing site to the mutation sequence can be set to the 3' end or inside the primer according to the specialty of the target sequence. The specificity of the primer can be adjusted by the length of the double-strand in the 3' end of the primer itself, if the target sequence has one or more bases mismatch to the primer, the loop-shaped structure of the primary can't be opened, the double-strand structure in the 3' end of the primer will be formed still and stop the 3' end extension ability, thus the amplification will not begin Referring to FIG. 2a and FIG. 2b.

Referring to FIG. 2a, according to the defects of rare mutation detecting in prior art, the present invention provides a method for detecting the rare mutation. According to FIG. 2a, the system of the invention comprises three primers, double amplification forward primer F, double amplification reverse primer R and universal tag primer T. In a preferred embodiment, the forward primer F has four different functional domains 11, 12, 13 and 14, herein the domain 11 is named target recognizing domain, domain 12 is named mutation recognizing domain, the mutation recognizing domain can be set in 3' end or away from the 3' end according to the types of the rare mutation, domain 13 is named tag sequence and the domain 14 is named complementary sequence. In a preferred embodiment, the antiforward primer R comprises three functional domains 13, 15 and 16, herein the domain 13 is named label sequence which has the same sequence with the domain 13 of the forward primer, domain 15 is named target combine domain, and domain 16 is named complementary sequence. In a preferred embodiment, the universal primer T is match to the domain 13 of forward primer F and the reverse primer R.

FIG. 2b shows the process of target amplification of the rare mutation by the primers of the invention. The amplification comprises two stages, in first stage, the target sequence containing rare mutation in a system with forward primer F and reverse primer R, in a high annealing temperature, preferably, the best annealing temperature is 60-66° C. The universal primer T has lower TM value in the temperature, so it can not match to the target sequence, while the forward primer F and reverse primer R can match to the target sequence 21 and 22 with high specificity, and extended to obtain sequence 23 and 24, the sequence 23 is match to reverse primer R in a high annealing temperature to extend to obtain sequence 25, thus achieve the accumulation of the rare mutation sequence. Because in high annealing temperature, the primer has lower combining efficiency to the target sequence, thus the accumulation in the stage can not obtain exponential accumulation with high efficiency.

In the second stage the universal primer T is used, the 3' end of the rare mutation sequence 25 accumulated in the first stage has sequence complementary to the universal primer T, in lower annealing temperature, preferably, the annealing temperature is 54-58, in this annealing temperature the universal primer T can be combined to the rare mutation sequence 25 with high efficiency, and extended to obtain sequence 26 containing rare mutation, both the sequence 25 and 26 can be match to the universal primer T, thus can be amplified exponentially, and obtain a large amount of sequence 27 containing rare mutation, therefore the amplification of the rare mutation sequence is achieved.

The Design Method of the Loop-Shaped Primers

Tm value of the domain combined to the target sequence: Tm value of the domain combined to the target sequence of the primer can be maintained in Tm value of general primer, this can be determined according to the containing of GC of the target sequence, commonly, the Tm value can be 55-65° C. The annealing temperature in amplification can have the same Tm value or 3-5° C. lower than the Tm value of the primer.

Tm value of the domain of the double-strand inside: generally, the complementary bases of the primer is 3-20 bp, the Tm value has same value with the amplification primer or 2-5° C. higher than the annealing temperature. According to the results of the preferred embodiments of the invention, if the loop-shaped primer is used for detecting a single base mutation by real-time PCR, the Tm value can be 3-5° C. higher than the annealing temperature. According to the primer for detecting rare mutation, the Tm value of the double-strand domain can be 5-12° C. higher than annealing temperature.

The site of the mutation recognizing base: according to general point mutation, the recognizing site can be set in the first base of 3' end of the primer; according to deletion mutation and insertion, the recognizing site can be several contiguous bases in the 3' end or near the 3' end; according to the condition that there may be the other similar mutations near the mutation position of the target gene, the mutation recognizing base can be set inside the primer, instead of the first base of the 3' end.

The length of the primer: generally, the total length of the primer is 20-80 bp, the target combination domain is 16-40 bp, the complementary domain inside, i.e. the double-strand domain, the 5' end and 3' end is 3-20 bp respectively, the loop-shaped domain is 5-60 bp, the universal label sequence is 16-30 bp.

The non-natural nucleic acid: any non-natural nucleic acid, e.g., LNA, PNA can be used in any site of the primer.

The best detecting structure of loop-shaped primer: the loop-shaped primer can be used for amplification detecting in real-time PCR. The amplifiers for the real-time PCR of the loop-shaped primer comprises: 7300, 7500, 7700 of Applied Biosystems (ABI), IQ Cycler of Bio-Rad, LightCycler2.0, LightCycler480 of Roche, Rotor-Gene 3000, 6000 of Corbett Research, MX3000P, MX3005P of Stratagene etc.

Advantages of the Loop-Shaped Primer

Simple design: The 3' end of the primer is a part of the target sequence, there are several bases in 5' end complementary to 3' end, the label sequence can be add or nor add inside the primer, the mutation recognizing base can be set in the first base of the 3' end or inside the primer, only the Tm value of the double-strand of the primer has the same temperature or higher than the annealing temperature in PCR system. By the teaching of the invention, any skilled person in the field can design the primer.

No primer dimers: before the temperature of pre-denaturation of PCR reach to denaturation temperature, because the double-strand of the primer itself closed the DNA extension ability; in the latter cycles of PCR, in conditions of maintaining in certain annealing temperature, the primer which can not combined to the target sequence will form an intra-molecular double-strand, and will not combine with another primer, thus primer dimers will not be produced.

High specificity: because the primer has a reverse complementary double-strand structure itself, only when the combination force of the target sequence combined with the target combination domain of the primer is stronger than the combination energy of the reverse complementary double-strand, the primer can hybridize with the target sequence, the loop-shaped structure can be opened, and the primer can obtain DNA extension ability. If there is any bases in target sequence which are not match to primer, e.g. single mismatch base, whether the mismatch position is in 3' end or inside the primer, the primer will maintain the loop-shaped structure at first, and the DNA extension ability of primer is then closed. In addition, because there is a reverse complementary structure in itself, the length of complementary domain can be adjusted to adjust the specification of the primer in design. To rare mutation, for example, somatic mutation in a background of larger amount wild-type DNA, the primer maintain the specification, except the sequence specification of 3'end is compete by complementary sequence.

High sensitivity: double amplification loop-shaped primer comprises universal tag sequence, so target sequence can be amplified for two stages. The mutation DNA has lower content in template, and the primer is in a background in larger amount of wild-type, thus the mutation amplification has lower efficiency, however, but if one copy is amplified, the target sequence will be rapidly amplified by the tag primer with high content in system.

Suitable for multiplex PCR system: because the primer can maintain high specificity itself and will not produce primer dimers, and has tag sequence, after two cycles of initial amplification, all the amplification product will be amplified by the same label sequence, thus avoid the problem that the different amplification efficiency of the primers and the problem of the primers effect to each other, so the primer of the invention is very suitable for multiplex PCR system, and suit for detecting system for multiple gene expression.

Suit for precise amplification for single mutation of mutation cluster region: the gene region which can produce mutation interested by researchers often densely produce mutations which have no relationship to the research, but the mutations are very similar to the mutations of interested to the researchers; in prior art, the specified base setting in the 3' end in ARMS easily caused cross reactions, while loop-shaped primer can set the specified base inside the primer and contain more target sequence domain, thus ensuring precise amplification. This is shown in FIG. 6.

Simple synthesis: Does not need any special machine, general DNA amplifiers can be used for synthesis.

Wide application field: it can be used to amplify difficult templates with high content of AT and high content of GC, and will detect point mutations, deletion mutations or insertion mutations.

PREFERRED EMBODIMENTS OF THE INVENTION

Embodiment 1

Loop-Shaped Primer Applied in Detecting the SUC2 of *Arabidopsis thaliana* by Real-Time PCR Based on Dyes To observe the primer dimers produced in real-time PCR system by the loop-shaped primer, a pair of primers according to SUC2 gene of *Arabidopsis thaliana* is designed, the amplification segment length is 100 bp, the PCR template is DNA extracted from the leaf tissue of *Arabidopsis thaliana*. The total volume is 50 µl, comprising: 5 µl 10×buffer (160 mM $[NH_4]_2SO_4$, 670 mM Tris-HCl pH 8.8, and 0.1% w/v Tween 20), 1.5 µl 25 mM $MgCl_2$, 400 µM each dNTP, 0.4 µM forward and reverse primer, Eve Green 0.5 µl, 1.0 U Taq DNA polymerase, 5 µl DNA template: the real-time PCR is processed in RotorGene 3000 Real-time PCR amplifier. The reaction condition is: 96° C. pre-denaturation for 3 min, 94° C. 3 min; 94° C. 15 s, 55° C. 20 s (detecting FAM fluorescence signal), 72° C. 15 s, 35 cycles; and then make resolution melting curve analysis. $H_2O$ is used as negative control. The loop-shaped primer comprises a nucleic acid sequence complementary to the amplification product. The forward primer is:

5'-AACCAGCTCATCGTCGCTGGAGCTGGTT-3 ' (SEQ ID NO:1), and the reverse primer is 5"-ATCAGCTTGCGGCGGTTTGTCAAGCTGAT-3' (SEQ ID NO:2), the bases with underline in the 5'end and 3' end are the bases formed the double strand region inside the primer.

Figure 1:
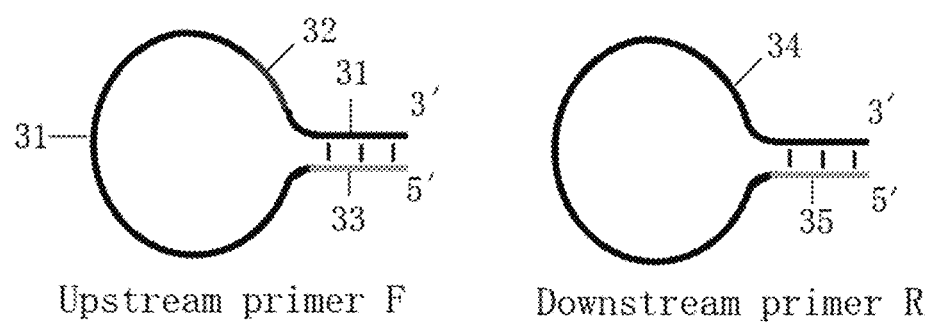
FIG. 1a shows the structure of single amplification loop-shaped primer.
FIG. 1b shows the reaction principle in PCR detecting of single amplification loop-shaped primer.
Figure 1B:
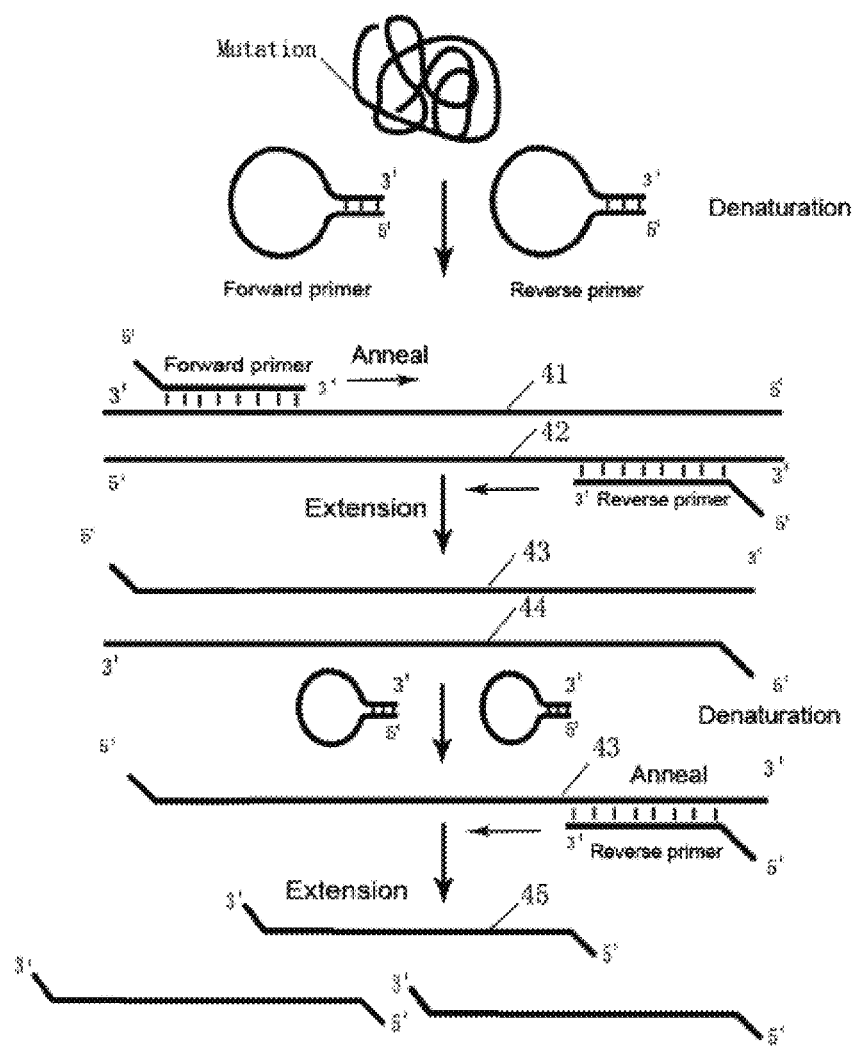
Figure 2A:
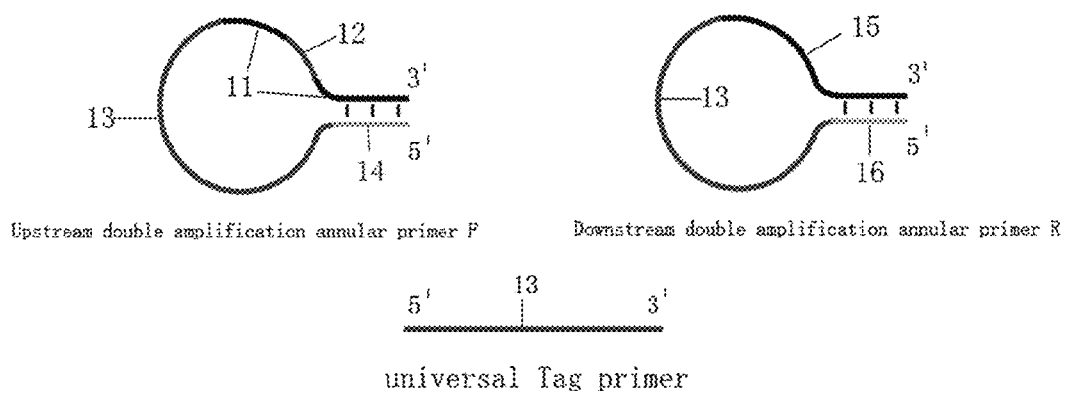
FIG. 2a shows the structure of double amplification loop-shaped primer.
Figure 2B:
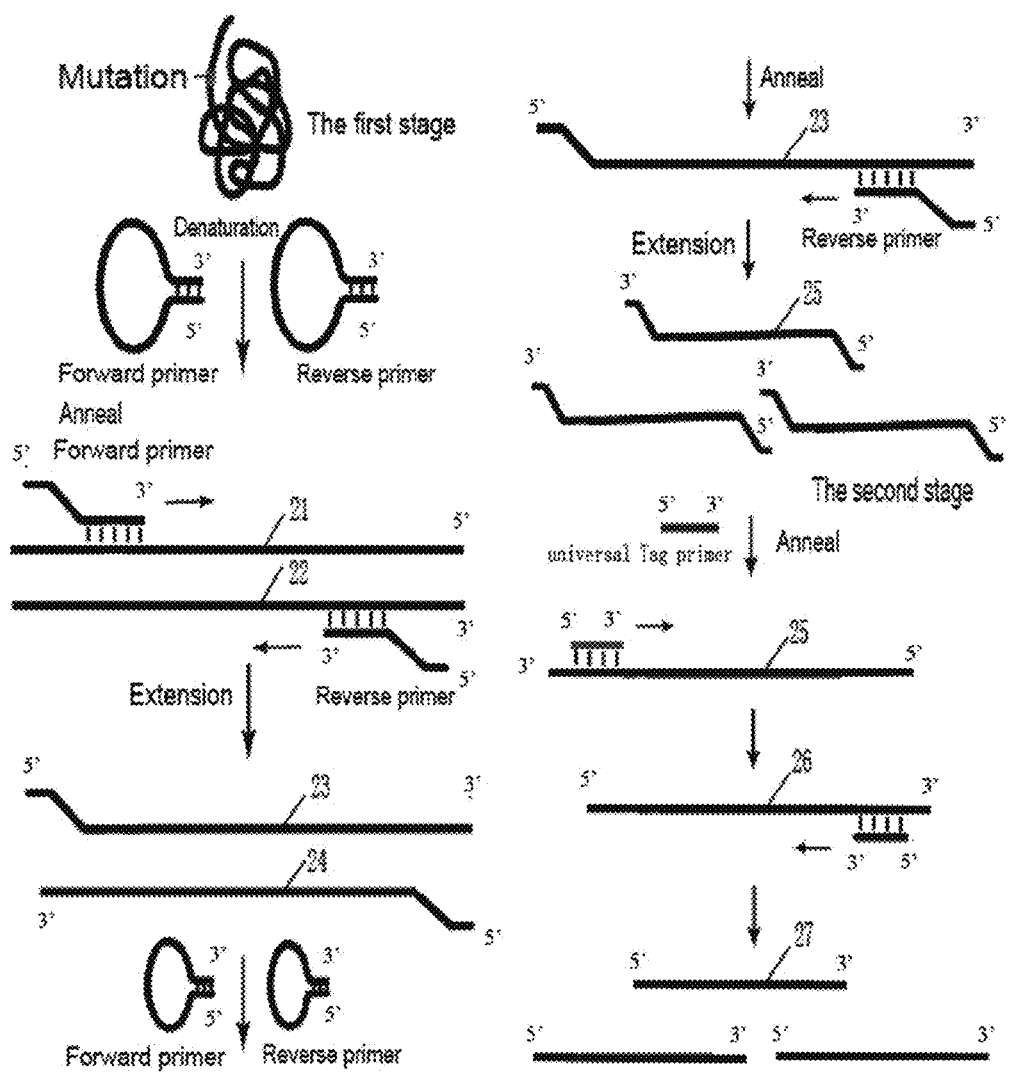
FIG. 2b shows the reaction principle in PCR detecting of double amplification loop-shaped primer.
Figure 3A:
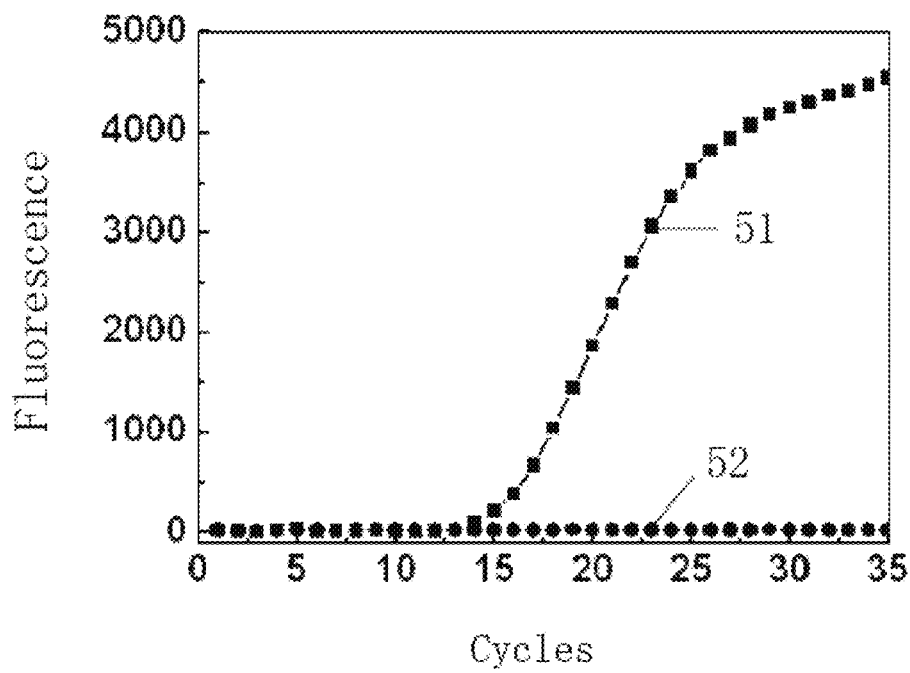
FIG. 3 shows the loop-shaped primer used in real-time PCR system based on fluorescent dyes in embodiments 1.

In PCR amplification, 35 cycles are detected by real-time fluorescence detecting and make resolution melting curve analysis, and the result is shown in FIG. 3

Referring to FIG. 3, herein 3a is a NTC (blank control) result of fluorescence PCR amplification of the primer of the present invention and the primer of prior art. Line 51 is NTC result of amplification of primer of prior art, and primer dimers can be seen obviously. Line 52 is NTC result of amplification of primer of the present invention, obviously, the primer of the present invention can effectively reduce the formation of primer dimers to avoid unnecessary amplification.

Figure 3B:
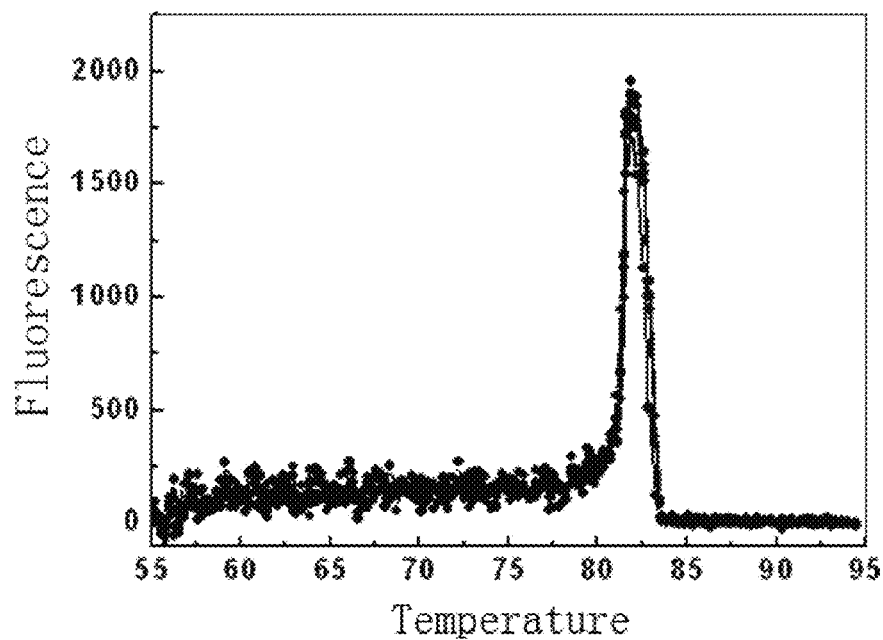

FIG. 3b is a resolution melting curve analysis result of the fluorescence PCR amplification of the primer of the present invention. Primer designed by prior art will form two peaks in curve because they form primer dimers: peak of primer dimers and peak of product. While the amplification by the primer of the present invention only form a peak of product.

Embodiment 2

Loop-Shaped Primer Cooperated with Probe Applied in Real-Time Quantity PCR for Detecting of HBV (Hepatitis B Virus)

To observe the effect of the primer of the present invention used in real-time PCR, the PCR template is a series of diluted standard DNA sample. Total reaction volume is 50 µl, comprises 5 µl 10×buffer (160 mM $[NH_4]_2SO_4$, 670 mM Tris-HCl pH 8.8, and 0.1% w/v Tween 20), 1.5 µl 25 mM $MgCl_2$, 400 µM each dNTP, 0.4 µM forward and reverse primer, 0.1 µM probe, 1.0 U Taq DNA polymerase, 5 µl DNA template. The real-time PCR is processed in Rotor-Gene 3000 Real-time PCR amplifier. The reaction condition is: 94° C. pre-denaturation for 5 min, 94° C. 15 s, 58° C. 25 s, 72° C. extension 15 s, 10 cycles; 94° C. 15 s, 58° C. 20 s (detecting FAM fluorescence signal), 72° C. 15 s, 35 cycles; and the standard DNA is diluted 10 times continuously. $H_2O$ is used for negative control. The loop-shaped primer comprises a nucleic acid sequence complementary to the amplification product. The forward and reverse primer amplified the S domain gene (NC-003977) of the HBV, and amplification for 174 bp. The forward primer is 5 '-GGTCCTACAACATCAGGATTCCVTAGGACC-3'(SEQ ID NO:3) and the reverse primer is 5'-CAACCTCGGTGAGTGATTGGAGGTTG-3' (SEQ ID NO:4), the target sequence of the probe is near to forward primer, the sequence is FAM-5 '-CAGAGTCTA-GACTCGTGGTGGACTTC-3"-BHQ (SEQ ID NO:5). The bases with underline in the 5'end and 3' end are the bases formed the double strand domain inside the primer.

Figure 4:
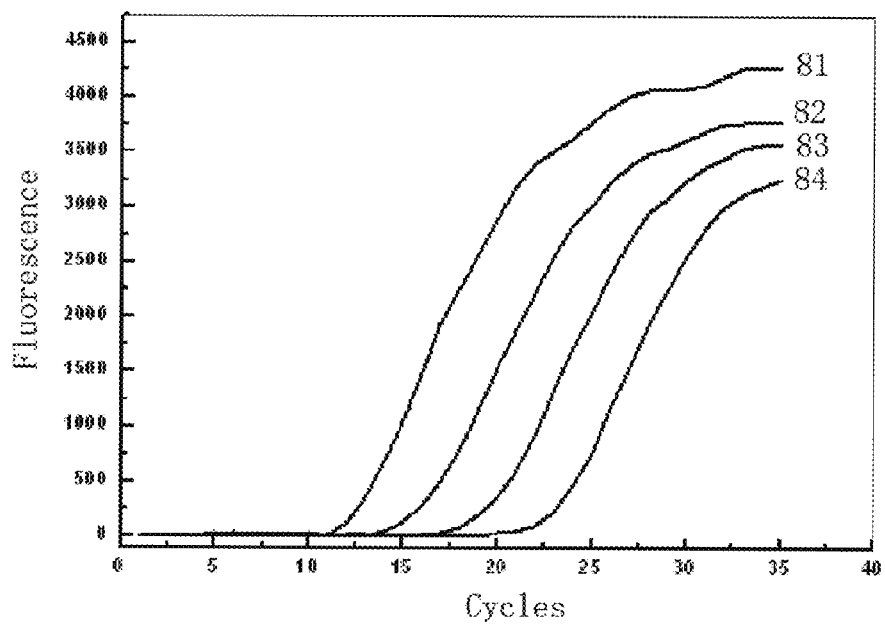
FIG. 4 shows the loop-shaped primer incorporated with probe used in real-time PCR in embodiment 2, the template is diluted to 10 times continuously.
Figure 5A:
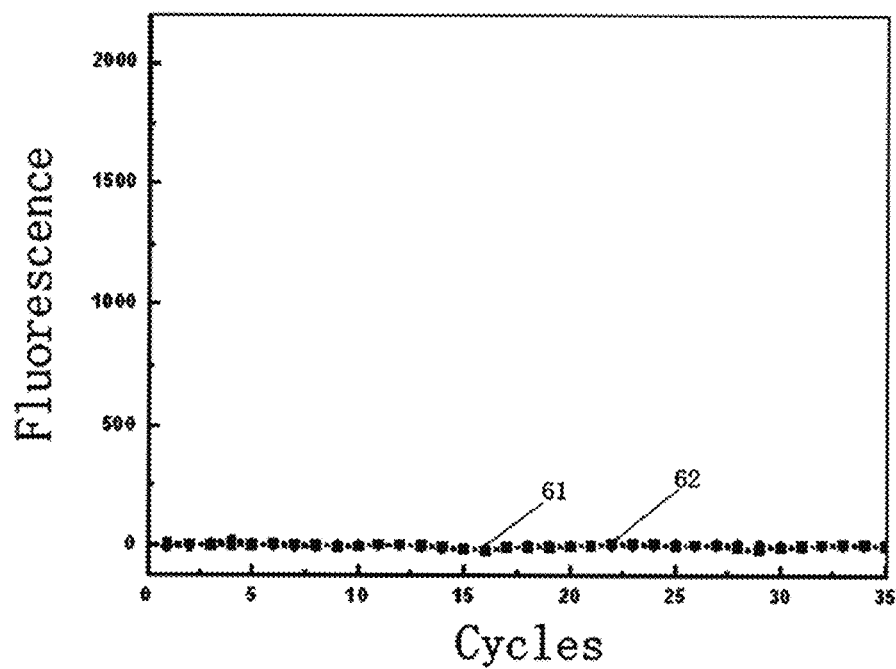
FIG. 5 shows the differentiate of the loop-shaped primer to SNP in embodiment 3.
Figure 5B:
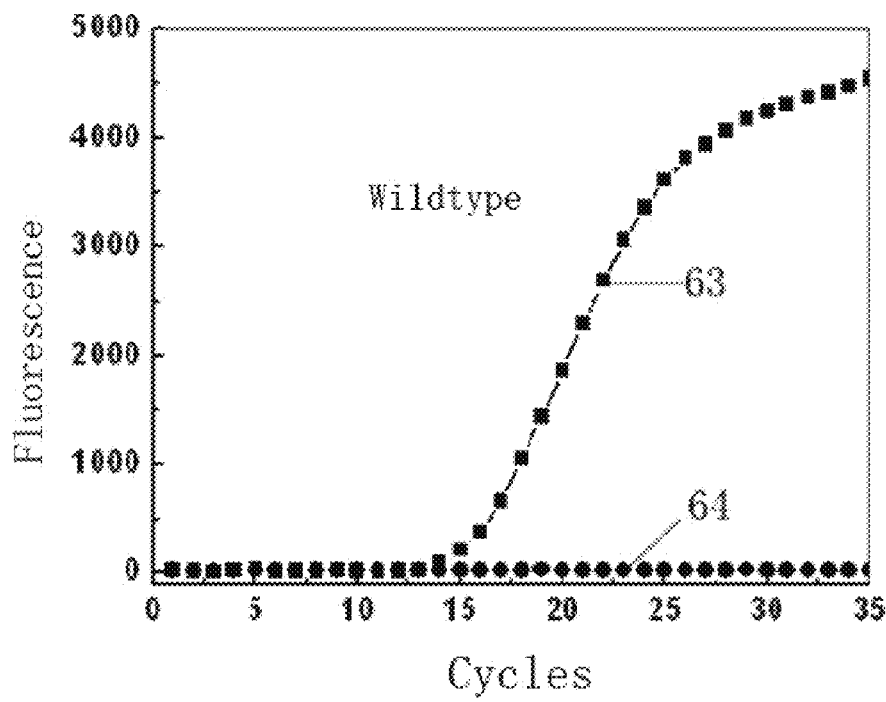
Figure 5C:
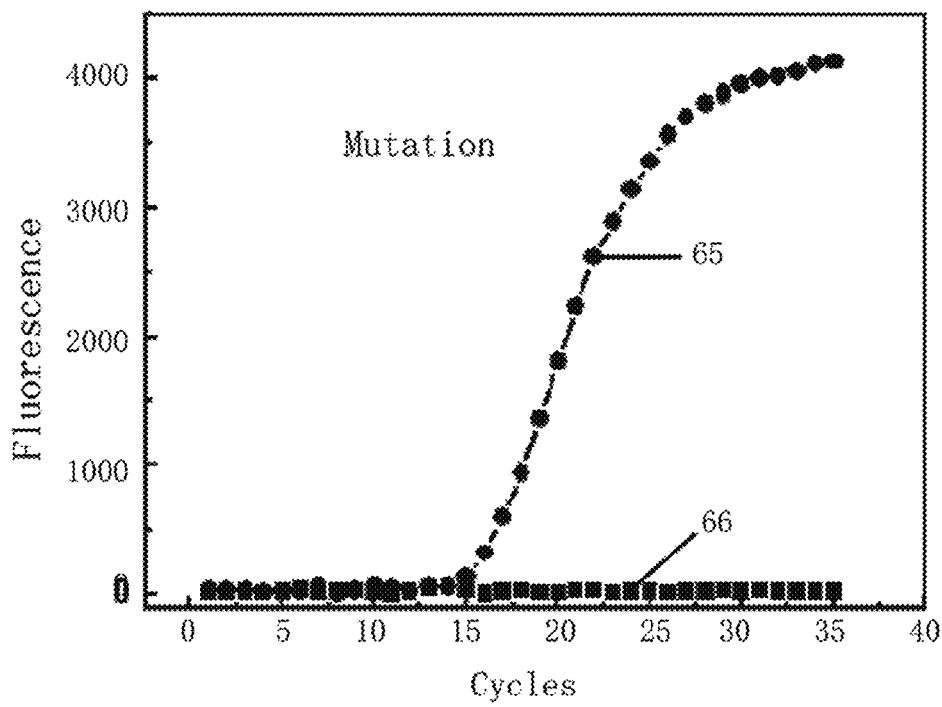
Figure 5D:
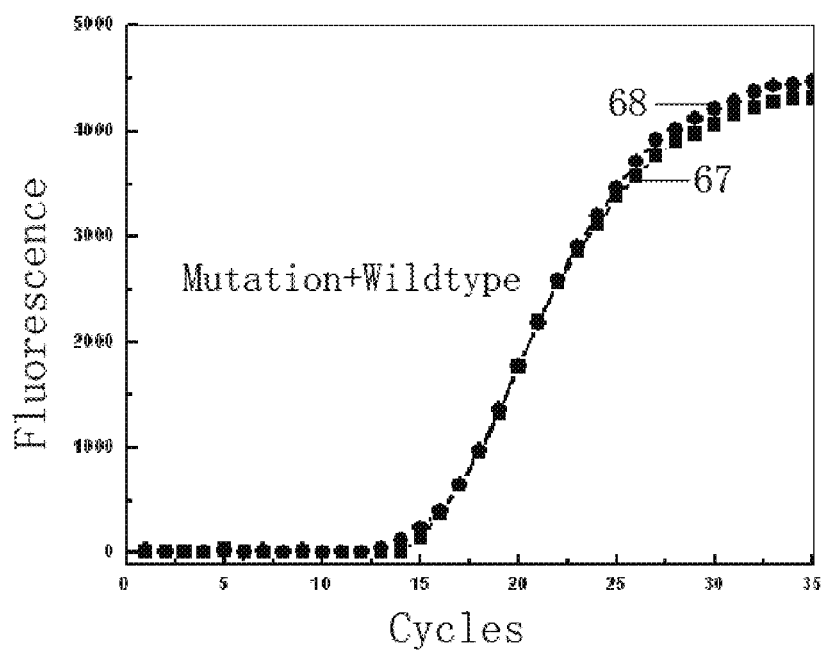

In PCR amplification, 35 cycles are detected by real-time fluorescence detecting, and the result is shown in FIG. 4. The initial concentration of target is line 81, line 82, 83, 84 shows the fluorescence curve of the template be diluted by 10 times diluted concentration in three continuously series respectively.

Embodiment 3

Detecting SNP by Loop-Shaped Primer of Real-Time PCR

HPA-4 of human platelet alloantigen (HPA) has a G>A mutation, it cause two platelet antigen HPA-4a and HPA-4b, herein HPA-4a is wild-type and HPA-4b is mutation type. According to these two antigens, a pair of loop-shaped primers are designed, the two primers only has a different base, and three typical samples with known gene type is selected to test. One is pure HPA-4a sample, the other is pure HPA-4b sample, and the third is a mixed type sample containing both HPA-4a and HPA-4b. In test a control sample. i.e. H$_2$O is used as negative. The primer for wild type HPA-4a is:

5'- CGCATCTG ACCAAGCTGGCCACCCAGATGC G-3' (SEQ ID NO:6), the primer for mutation type HPA-4b is 5'- CGCATCTG ACCAAGCTGGCCACCCAGATGC A-3' (SEQ ID NO:7), the base with underline is a mutation base, the bases with frame are bases in loop-shaped combination domain. The universal reverse primer is 5'-TGC-CCCGAAGCCAATCC-3' (SEQ ID NO:8).

The reaction includes two PCR, one contains wild-type primer, another contains mutation type primer. The total reaction volume is 25 μL, comprises 2.5 μl 10× buffer (160 mM [NH$_4$]$_2$SO$_4$, 670 mM Tris-HCl pH 8.8, and 0.1% w/v Tween 20), 1.5 μl 25 mM MgCl$_2$, 400 μM each dNTP, 0.4 μM primers, 0.5 μl Eve Green, 1.0 U Taq DNA polymerase, 20 ng DNA template. The real-time PCR is processed in RotorGene 3000 Real-time PCR amplifier. The reaction condition is: 96° C. pre-denaturation for 2 min, then 96° C. denaturation 15 s, 68° C.-59° C. 15 s (after each cycle, the temperature fall 1° C.), 72° C. extension 15 s, 10 cycles; 94° C. 3 min; 94° C. 15 s, 58° C. 20 s (detecting FAM fluorescence signal), 72° C. 15 s, 35 cycles totally.

FIG. 5 shows the result of SNP of real-time fluorescence detecting, the result includes two PCR, one is aimed to wild-type and the other is aimed to mutation type. The amplification result according to wild-type is shown in solid square, and the amplification result according to mutation-type is shown in solid circle.

Relative to negative sample, both the wild-type primer (line 61) and the mutation-type primer (line 62) has no amplification product. The results show that only when the template is in the reaction system, the corresponding amplification will process. When both the two target sequence are in samples, the products of the wild-type primer (line 67) and the mutation-type primer (line 68) are markedly increase. However, according to wild-type target, the increase of the product is caused by the amplification of the wild-type primer (line 63) not by the amplification of the mutation-type primer (line 64). In reverse, according to mutation-type target, the increase of the product is caused by the amplification of the mutation-type primer (line 65) not by the amplification of the wild-type primer (line 66). This proved that the primer of the invention differentiate the target by one or more nucleic acid. When there is not template, not amplification is found, when there are two templates, amplification signals of both two PCR are found.

Embodiment 4

Double Amplification Loop-Shaped Primer Used in Precise Amplification for Single Rare Mutation of Mutation Cluster Region of Codon 12 of K-ras K-ras gene has important functions in cell growth and differentiation, there are about 70% of cancers relates to the 12, 13 codons mutation, the other codon mutation happen in 59 and 61 site. each base of the three bases in the 12 or 13 codon may be mutation, generally, the mutation is happen in the first or the second bases, it may be mutated to be the other three bases except itself, or both the first and second bases may be mutated. For example, the first base of the codon 12 is mutate to A, i.e. GGT>TGT (Cosmic ID:480) this mutation is a hotspot mutation relating to the drug-resistant to the Erbitux, a drug for treating colon cancer; while both the first and second bases mutated, e.g. GGT>TGC (Cosmic ID:513), GGT>TTT (Cosmic ID:512), GGT>TAT (Cosmic ID:25081), these three mutations are common mutation, and are not sure whether they are relating to drug-resistant to the Erbitux. Common ARMS primer are easily detecting these mutations as GGT>TGT in mistake.

According to the wild-type and mutation sequence GGT>TGT (Cosmic ID:480) of codon 12 publicized by Cosmic, a pair of double amplification loop-shaped primer and a probe are designed, which are K-ras-M1-F, K-ras-M1-R, K-ras-P respectively. According to wild-type gene of HGH publicized by Cosmic, a pair of double amplification loop-shaped primers and a probe are designed as HGH-F, HGH-R, HGH-P respectively.

The method of detecting the GGT>TGT mutation of K-ras of clinical paraffin-bended tissue sample by above PCR system comprises the following steps:

(1) sample treating and template extraction: clinical paraffin-bended tissue samples are sliced to 5-10 μm, and 1 ml xylene is added to remove the paraffin, collect deposit by centrifuge, and add 1 ml absolute ethanol in the deposit, dry in room temperature or 37° C., add protease K and Buffer ATL, 56° C. digest for 1 h, 90° C. incubate for 1 h, add 200 ml Buffer AL and blending, then add 200 μl absolute ethanol and blend, the supernatant is carefully removed to QIA 2 ml spin column, 6000×g (8000 rpm) 1 min, then add 500 μl Buffer AW1, 6000×g (8000 rpm) 1 min, carefully open the cover and add 500 μl Buffer AW2, 6000×g (8000 rpm) 1 min, the empty tube centrifuge in 20000×g (14000 rpm) for 3 min, add 100 μl Buffer ATE in the middle of film, incubate for 5 min, 20000×g (14000 rpm) 1 min. take 3 3 μl to detect OD value, the DNA sample is diluted to 2 ng/μl, take 5 μl for PCR (2) Fluorescence PCR amplification system comprising:

| 1 × PCR buffer | |
|---|---|
| MgCl$_2$ | 7.0 mmol |
| dNTP each | 1.0 mmol |
| primers | 0.5~1.0 μmol |
| label sequence T | 5~10 μmol |

-continued

| 1 × PCR buffer | |
|---|---|
| probes | 0.5~1.0 μmol |
| Taq polymerase | 1.0 U |
| template | 5 μl |
| total volume | 25 μl |

Sequence of the Primers and the Probe
K-ras-M1-F: ACAAGCTCCGCAAGGGGTCAGTAAAGCGAAACTTGTGGTAGTTGGAGCTTGT (SEQ ID NO:9), herein the bases with underline are label sequence, the bases with frame in 5' end are complementary to the bases in 3' end, the bold bases are the mutation recognizing base; K-ras-M1-R: GCAAGGGGTCAGTAAAGCGTCGTCCACAAAATGATTCTG (SEQ ID NO:10), herein the bases with underline are label sequence, the label sequence T is GCAAGGGGTCAGTAAAGCG (SEQ ID NO:11). K-ras-P: FAM-5' TGCCTTGACGATACAGCT3'-BHQ (SEQ ID NO:12). The inner control system HGH-F: 5'-GCAAGGGGTCAGTAAAGCGGCAGTGCCTTCCCAACCATT-3' (SEQ ID NO:13), HGH-R: 5'-GCAAGGGGTCAGTAAAGCGCATTCCCCAAGAGCTTACAAACTC-3' (SEQ ID NO:14), herein the bases with underline are label sequence, HGH-P: HEX-5'TTGACAACGCTATGCTCCGC3'-BHQ (SEQ ID NO:15).

The reaction condition of real-time PCR is: 96° C. predenaturation for 3 min 15 cycles, then 95° C. denaturation 15 s, 64° C. 25 s, 72° C. extension 10 s, 35 cycles; 95° C. 15 s; 58° C. 25 s, 72 (detecting FAM fluorescence signal), 72° C. 15 s, ° C. extension 10 s, 35 cycles. The final 35 cycles are detected the FAM and HEX signals in annealing steps.

(3) detection: the fluorescence is detected in annealing stage by MX3000p real-time PCR Amplifier (SRATGENE), the PCR tube containing reaction liquid is detected one by one in the fluorescence PCR Amplifier.

Result judge: according to the Ct value shown on the fluorescence PCR Amplifier to detect the FAM and HEX fluorescence intensity in the reaction system, HEX signal reach to threshold (Ct>18) means that the DNA content is within limit, and the FAM signal result is reliable; by whether the FAM signal is arise as the judgment of negative and positive, the PCR amplification curve with normal S-shape is positive.

(4) Specification Analysis

Specification detecting: DNA of the cell SW48 is taken as control, the collected sample is detected for GTG>TGT mutation of K-ras, the result shows that only the sample containing GTG>TGT mutation of K-ras has fluorescence signal, while the DNA of the cell SW48 used as control has no fluorescence signal. In addition, 100 samples from blood bank are used to further identify the specification of the fluorescence PCR. The results show that the blood samples from blood bank has no fluorescence signal detecting by fluorescence PCR.

(5) Sensitivity Analysis

The quantitative analysis is processed by synthetic plasmid DNA which containing GTG>TGT mutation of K-ras, take the sample DNA with content of 1000 copies after quantify and diluted 10 times, and take three diluted grades, then take 5 μl in each of four diluted grades, eight parallel groups are used to fluorescence PCR. The method of the present invention has high sensitivity, 1-10 copys/μl can be detected out.

Figure 6:
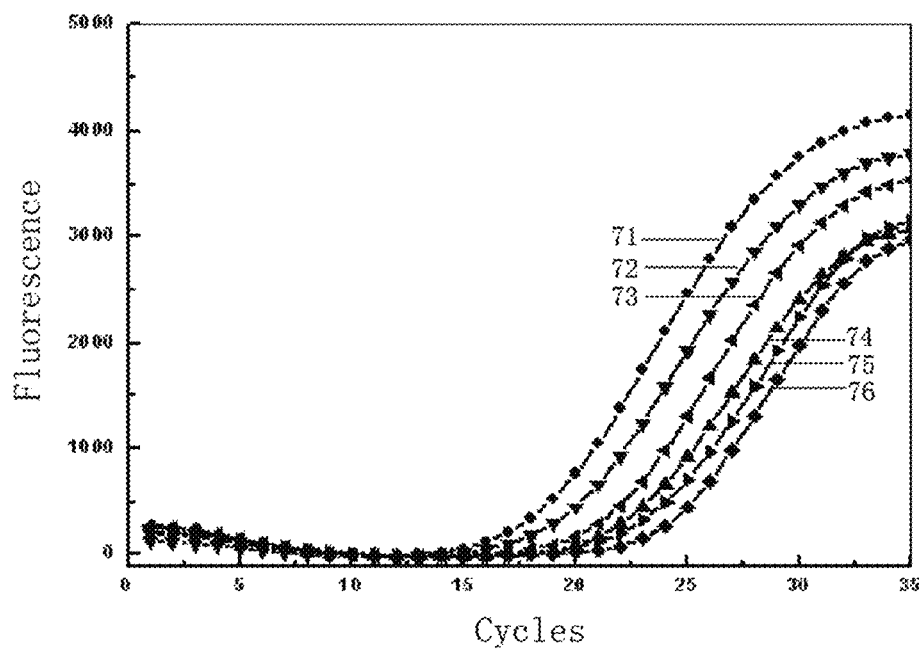
FIG. 6 shows precise amplification for single rare mutation of mutation cluster region by double amplification loop-shaped primer in embodiment 4.

(6) Selectivity 5 copies of synthetic plasmid DNA which containing GTG>TGT mutation of K-ras are fluorescence detected in background of 1 ng, 5 ng, 10 ng, 50 ng, 100 ng, 200 ng, shown in FIG. 6

FIG. 6 shows the detecting result of amplification for rare mutation template in different content background by the double amplification loop-shaped primer of the present invention. the mutation template is detected in background of 1 ng, 5 ng, 10 ng, 50 ng, 100 ng, 200 ng respectively, line 71 is 5 copy in 1 ng background, line 72 is 5 copy in 5 ng background, line 73 is 5 copy in 10 ng background, line 74 is 5 copy in 50 ng background, line 75 is 5 copy in 100 ng background, and line 76 is 5 copy in 200 ng background The result show that the double amplification loop-shaped primer of the present invention has high selectivity.

What is claimed is:

What is claimed is:

1. A method of amplifying a nucleic acid, comprising initially denaturing a target sequence containing a mutation sequence, as well as a forward primer and a reverse primer respectively having a target recognizing sequence and complementary sequences on both 3' end and 5' end thereof to form a single-loop structure having a blunt end before denaturing, wherein the forward primer further has a mutation recognizing sequence for recognizing the mutation sequence;
　　annealing the forward primer and the reverse primer with the target sequence;
　　extending the forward primer and the reverse primer along the target sequence;
　　denaturing the target sequence, as well as the extended forward and reverse primers, wherein the sequence extended from the forward primer is an object sequence to be amplified by a subsequent polymerase chain reaction (PCR) and wherein the method excludes use of DNA helicase.

2. The method of claim 1, wherein the mutation recognizing sequence is located on the first base of the 3' end of the forward primer when the mutation sequence of the target sequence is a point mutation.

3. The method of claim 1, wherein the mutation recognizing sequence has several contiguous bases in the 3' end or near the 3' end when the mutation sequence of the target sequence is a deletion or insertion mutation.

4. The method of claim 1, wherein a total length of the forward and reverse primers is 20-80 base pairs.

5. The method of claim 1, wherein a length of the complementary sequences on the 3' and 5' ends of the forward and reverse primers is 3-20 base pairs.

6. The method of claim 1, wherein the forward and the reverse primers comprise at least a non-natural nucleic acid.

7. A method of amplifying a nucleic acid, comprising initially denaturing a target sequence containing a mutation sequence, a tag primer having a tag sequence, as well as a forward primer and a reverse primer respectively having a tag sequence and complementary sequences on both 3' end and 5' end thereof to form a single-loop structure having a blunt end before denaturing, wherein the tag primer has a lower melting temperature than the melting temperature of the forward and reverse primers, wherein the forward primer further has a target recognizing sequence and a mutation recognizing sequence for recognizing the mutation sequence, and wherein the reverse primer further has a target combine sequence;
　　annealing the forward primer and the reverse primer with the target sequence;
　　extending the forward primer and the reverse primer according to the target sequence;
　　denaturing the target sequence, as well as the extended forward and reverser primers to obtain a first object sequence extended from the forward primer;
　　annealing the first object sequence and the reverse primer;
　　extending the reverse primer along the first object sequence to obtain a second object sequence extended from the reverse primer;
　　amplifying the second object sequence by the tag primer by a subsequent polymerase chain reaction (PCR) wherein the melting temperature of the complementary sequences when in the single-loop structure is higher than the annealing temperature.

8. The method of claim 7, wherein the mutation recognizing sequence is located on the first base of the 3' end of the forward primer when the mutation sequence of the target sequence is a point mutation.

9. The method of claim 7, wherein the mutation recognizing sequence has several contiguous bases in the 3' end or near the 3' end when the mutation sequence of the target sequence is a deletion or insertion mutation.

10. The method of claim 7, wherein a total length of the forward and reverse primers is 26-80 base pairs.

11. The method of claim 7, wherein a length of the complementary sequences on the 3' and 5' ends of the forward and reverse primers is 3-26 base pairs.

12. The method of claim 7, wherein the forward and the reverse primers comprise at least a non-natural nucleic acid.

* * * * *